(12) United States Patent
Phelps et al.

(10) Patent No.: US 7,794,400 B2
(45) Date of Patent: *Sep. 14, 2010

(54) ELEMENT MAPPING AND TRANSMITTER FOR CONTINUOUS WAVE ULTRASOUND IMAGING

(75) Inventors: Robert N. Phelps, Sammamish, WA (US); David A. Petersen, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1463 days.

This patent is subject to a terminal disclaimer.

(21) Appl. No.: 10/787,672

(22) Filed: Feb. 26, 2004

(65) Prior Publication Data

US 2005/0203391 A1 Sep. 15, 2005

(51) Int. Cl.
*A61B 8/00* (2006.01)
(52) U.S. Cl. .................................. 600/459; 73/596
(58) Field of Classification Search ............... 600/449, 600/447, 472; 73/596
See application file for complete search history.

(56) References Cited

U.S. PATENT DOCUMENTS

| | | | |
|---|---|---|---|
| 5,155,492 A * | 10/1992 | Hopwood et al. ........... 342/372 |
| H001171 H | 4/1993 | Fillhart | |
| 5,267,221 A | 11/1993 | Miller et al. | |
| 5,348,014 A | 9/1994 | Okado | |
| 5,522,393 A | 6/1996 | Phillips et al. | |
| 5,538,004 A | 7/1996 | Bamber | |
| 5,555,534 A * | 9/1996 | Maslak et al. ............... 367/135 |
| 5,573,001 A | 11/1996 | Petrofsky et al. | |
| 5,590,658 A | 1/1997 | Chiang et al. | |
| 5,617,866 A | 4/1997 | Marian | |
| 5,622,177 A | 4/1997 | Breimesser et al. | |
| 5,627,536 A | 5/1997 | Ramirez | |
| 5,676,147 A | 10/1997 | Petrofsky | |
| 5,690,114 A | 11/1997 | Chiang et al. | |
| 5,817,024 A | 10/1998 | Ogle et al. | |
| 5,820,549 A | 10/1998 | Marian | |
| 5,839,442 A | 11/1998 | Chiang et al. | |

(Continued)

FOREIGN PATENT DOCUMENTS

CN 1342442 4/2002

(Continued)

OTHER PUBLICATIONS

Office Action dated Oct. 5, 2007, for US 2005-0148873 (U.S. Appl. No. 10/741,538).

(Continued)

*Primary Examiner*—Brian Casler
*Assistant Examiner*—Parikha S Mehta

(57) ABSTRACT

Element mapping and transmission of continuous waves are provided ultrasound imaging. For use with multiple dimensional or large arrays, the number of receive beamformer channels or associated cables connecting the transducer array to the receive beamformer may be limited. Subarrays of signals from different elements associated with similar phasing are combined without switching. The combined subarray signals are then received beamformed to generate a continuous wave image. Receive channels without clocking or beamforming prior to a steered continuous wave Doppler beamformer maximize dynamic range and reduce the power consumption. For further or different optimization of steering continuous waves, low voltage transmitters separate from high voltage transmitters are provided for a plurality of elements.

28 Claims, 5 Drawing Sheets

U.S. PATENT DOCUMENTS

| | | | |
|---|---|---|---|
| 5,957,846 A | 9/1999 | Chiang et al. | |
| 5,964,709 A | 10/1999 | Chiang et al. | |
| 5,997,479 A | 12/1999 | Savord et al. | |
| 6,013,032 A * | 1/2000 | Savord | 600/443 |
| 6,016,285 A | 1/2000 | Wright et al. | |
| 6,029,116 A | 2/2000 | Wright et al. | |
| 6,102,863 A | 8/2000 | Pflugrath et al. | |
| 6,106,472 A | 8/2000 | Chiang et al. | |
| 6,126,602 A | 10/2000 | Savord et al. | |
| 6,126,606 A | 10/2000 | Bergstoel | |
| 6,142,946 A | 11/2000 | Hwang et al. | |
| 6,238,346 B1 * | 5/2001 | Mason | 600/459 |
| 6,248,073 B1 | 6/2001 | Gilbert et al. | |
| 6,371,918 B1 | 4/2002 | Bunce | |
| 6,375,617 B1 | 4/2002 | Fraser | |
| 6,380,766 B2 * | 4/2002 | Savord | 327/108 |
| 6,491,634 B1 | 12/2002 | Leavitt et al. | |
| 6,527,722 B1 | 3/2003 | Fazioli et al. | |
| 6,530,887 B1 | 3/2003 | Gilbert et al. | |
| 6,540,685 B1 | 4/2003 | Rhoads et al. | |
| 6,544,175 B1 | 4/2003 | Newman | |
| 6,575,908 B2 | 6/2003 | Barnes et al. | |
| 6,582,367 B1 | 6/2003 | Robinson et al. | |
| 6,589,179 B2 | 7/2003 | Criton et al. | |
| 6,612,987 B2 | 9/2003 | Morsy et al. | |
| 6,629,928 B1 | 10/2003 | Dolan et al. | |
| 6,635,019 B2 * | 10/2003 | Davidsen | 600/459 |
| 6,648,826 B2 | 11/2003 | Little et al. | |
| 6,814,701 B1 | 11/2004 | Tamura | |
| 6,875,178 B2 | 4/2005 | Phelps et al. | |
| 6,932,517 B2 | 8/2005 | Swayze et al. | |
| 7,169,108 B2 | 1/2007 | Little et al. | |
| 7,371,218 B2 | 5/2008 | Walston et al. | |
| 2003/0139664 A1 | 7/2003 | Hunt et al. | |
| 2004/0002435 A1 | 1/2004 | Petersen et al. | |
| 2004/0109028 A1 | 6/2004 | Stern et al. | |
| 2004/0181154 A1 | 9/2004 | Peterson et al. | |
| 2005/0148873 A1 | 7/2005 | Petersen et al. | |
| 2005/0148878 A1 | 7/2005 | Phelps et al. | |
| 2005/0192499 A1 | 9/2005 | Lazenby et al. | |
| 2005/0203391 A1 | 9/2005 | Phelps et al. | |
| 2008/0027322 A1 | 1/2008 | Freiburger | |
| 2008/0027323 A1 | 1/2008 | Freiburger | |

FOREIGN PATENT DOCUMENTS

| | | |
|---|---|---|
| WO | 00/30540 | 6/2000 |

OTHER PUBLICATIONS

"Fully Sampled Matrix Transducer for Real Time 3D Ultrasonic Imaging," by Savord, et al., Phillips Medical Systems, 300 Minuteman Rd., Andover, MA., 9 pgs., before Dec. 2003.

* cited by examiner

ELEMENT MAPPING AND TRANSMITTER FOR CONTINUOUS WAVE ULTRASOUND IMAGING

BACKGROUND

The present invention relates to continuous wave ultrasound imaging. In particular, transmitters and channel count reduction are provided for steered continuous wave Doppler ultrasound imaging.

To reduce the channel count, signals from different elements are combined to form subarrays. The use of subarrays may minimize the number of receive beamformer channels used in an ultrasound imaging system or the number of cables to communicate the signals from the elements to the ultrasound imaging system. For example, a two-dimensional transducer array is divided into a number of pre-set subarrays. Signals from elements within a same subarray are combined together and transmitted through a cable to an ultrasound imaging system. The number of subarrays corresponds to the number of cables and receive beamformer channels of the imaging system. However, the subarrays may change with different steering.

U.S. application Ser. Nos. 10/741,827 and 10/741,538, the disclosures of which are incorporated herein by reference, disclose altering the size of subarrays as a programmable trade off between the number of transducer array elements and the number of receive beamformer channels. The size, shape or location of subarrays may be dynamically varied. Electronics are provided in the transducer assembly for implementing the subarray variation. The electronics provide time division multiplexing or partial beamforming for the subarrays. The electronics allow variation in subarray size for use with a same ultrasound imaging system.

Time division multiplexing or partial beamforming are implemented with clocked circuits or switching applied to receive signals. Other partial beamforming within a transducer probe includes charge coupled device delay lines or linear phased switched capacitors. Switching limits the dynamic range of the signal. For pulsed wave imaging, the dynamic range limitations may be acceptable. However, for continuous wave imaging, the limits on dynamic range from switching may be unacceptable.

Switching also dissipates power. Power consumption for switching may result in less power for preamplification. Power is also used to continuously generate waveforms. Less power for preamplification reduces the amount of available dynamic range.

Similarly, the transmitters used for pulsed wave imaging use high voltage sources with a low duty cycle. The transmitters are also used for continuous wave imaging by reducing the voltage, resulting in poor power dissipation. Using a large number of high voltage transmitters for continuous wave transmission with a multidimensional array exacerbates power dissipation problems.

BRIEF SUMMARY

By way of introduction, the preferred embodiments described below include methods and systems for element mapping and transmission of continuous waves in ultrasound imaging. For use with multiple dimension or large arrays, the number of receive beamformer channels or associated cables connecting the transducer array to the receive beamformer may be limited. Subarrays of signals from different elements associated with similar phasing are combined without switching. The combined subarray signals are then received beamformed to generate a continuous wave image. Receive channels without clocking or beamforming prior to a steered continuous wave Doppler beamformer maximize dynamic range. For further or different optimization of steering continuous waves, low voltage transmitters separate from high voltage transmitters are provided for a plurality of elements.

Various aspects and advantages are provided in the preferred embodiments. In a first aspect, a system for selecting subarrays in continuous wave imaging is provided. A transducer array is provided as part of a transducer assembly. The transducer array has a plurality of elements. A plurality of combiners is operable to combine signals from a respective plurality of subarrays of the plurality of elements. Channels from the plurality of elements to the plurality of combiners are free of switching during reception of continuous wave signals.

In a second aspect, a method for selecting subarrays is provided for continuous wave ultrasound imaging. Continuous wave signals from a first plurality of elements are summed. The summed signals correspond to a first range of phase shifts. Continuous wave signals from a second plurality of elements are summed. The summed signals correspond to a second range of phase shifts different than the first range. The outputs from the two summing operations are transmitted separately to a receive beamformer.

In a third aspect, a system for transmission of continuous waves in ultrasound imaging is provided. A pulse wave transmitter is connectable with a transducer array. A continuous wave transmitter is also connectable with the transducer array. The continuous wave transmitter is separate from the pulse wave transmitter.

In a fourth aspect, a method is provided for transmission of continuous waves in ultrasound imaging. Continuous waves are generated with the continuous wave transmitter separate from a pulse wave transmitter. The continuous waves are applied to a transducer array within a same probe housing as the continuous wave transmitter.

The present invention is defined by the following claims, and nothing in this section should be taken as a limitation on those claims. Further aspects and advantages of the invention are disclosed below in conjunction with the preferred embodiments. The aspects discussed above or further aspects disclosed below may be later claimed independently or in combination.

BRIEF DESCRIPTION OF THE DRAWINGS

The components and the figures are not necessarily to scale, emphasis instead being place upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Steered continuous wave Doppler imaging may be optimized by providing a wide dynamic range. Minimizing noise while maximizing the dynamic range is provided through careful design of grounding, clocking and quantization. For multi-dimensional or large arrays used for two- or three-dimensional imaging, the number of signals provided from a transducer to a receive beamformer is reduced to minimize receive beamformer circuitry costs and cable counts. By combining signals from different elements with similar phases without clocking or other beamforming within the transducer assembly, the signals from a large number of elements are transmitted to an imaging system for steering continuous wave beamformation. For transmissions, a separate continuous waveform transmitter is provided. In one embodiment, the transmitter is used with the similar phase shift subarray combination, but the two aspects may be used independently in different embodiments.

Figure 1:
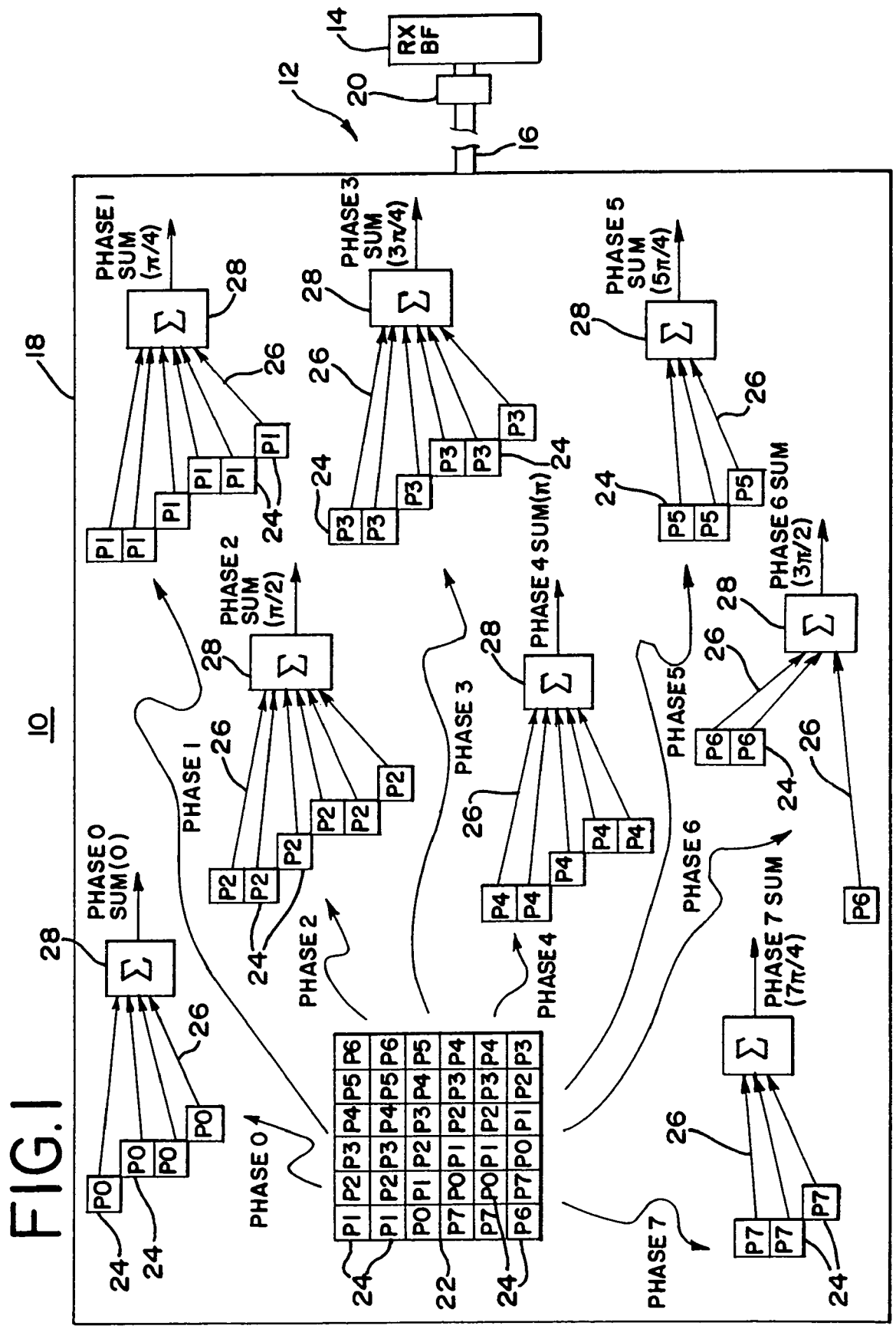
FIG. 1 is a graphical representation of a continuous wave reception system and combination of signals with similar phase in one embodiment.

FIG. 1 shows one embodiment of a system 10 for selecting subarrays in continuous wave ultrasound imaging. The system 10 includes a transducer assembly 12 releasably connectable with an imaging device and associated receive beamformer 14. Additional, different or fewer components may be provided. While shown as separable, the transducer assembly 12 may be permanently connected with the receive beamformer 14. In other embodiments, a portion of or the entire receive beamformer 14 is located within the transducer assembly 12.

The transducer assembly 12 includes a cable 16 connecting a probe housing 18 to a connector 20. Additional, different or fewer components may be provided, such as the probe housing 18 including the connector 20 without the cable 16. The cable 16 is a plurality of coaxial cables connecting the probe housing to the receive beamformer 14 through the connector 20. The connector 20 is any now known or later developed mechanical and electrical structure for releasably connecting the transducer probe assembly 12 with an ultrasound imaging device.

The transducer probe housing 18 is plastic, metal, epoxy, polymer, fiberglass or other now known or later developed structures for housing a transducer array 22. The probe housing 18 is shaped for ergonomic use within a hand, such as for holding a transducer probe adjacent to a skin or outer surface of a patient. In other embodiments, the transducer probe housing 18 is shaped for use internal to a patient, such as a catheter or endocavity probe.

The transducer array 22 is a one or multi-dimensional transducer array of elements. For a multi-dimensional array, the elements are spaced along a rectangular, square, hexagonal, triangular or other now known or later developed grid pattern. The grid pattern is either fully sampled or sparsely sampled. The transducer array 22 is planar but may be curved along one or more dimensions. The transducer array 22 is at least partially within or is a part of the transducer probe assembly 12. As shown in FIG. 1, the transducer array 22 is within the transducer probe housing 18. Either through an opening or an acoustic window or lens in the transducer probe housing 18, the transducer array 22 transmits and receives acoustical energy.

The transducer array 22 has a plurality of elements 24. Each of the elements 24 is a piezoelectric or capacitive membrane transducer. Other now known or later developed transducers may be used. Each element 24 is associated with two electrodes for transducing between electrical and acoustical energies. While thirty-six elements 24 are shown in the array 22, a greater or fewer number elements may be used. The elements 24 are labeled P0 through P7. The labels correspond to different amounts of relative phase shift. For steering continuous wave signals received by each of the elements, a relative phasing is applied to the signals by the receive beamformer 14. As the depth of focus or focus location changes, the phasing relationship between elements may change.

The probe housing 18 of FIG. 1 is shown populated by a plurality of different groupings of elements 24. Arrows from the array 22 to the different groupings of elements 24 conceptually represent a switch distribution of elements 24. In steered continuous wave beamforming, range information is not used based on the time of signal returned. Steered continuous wave beamforming is used to detect frequency shifts imparted upon the transmitted pressure wave due to moving objects. The stability of moving objects relative to the frequency of the ultrasound waves and the speed of sound in the tissue allows for delays to wrap once they exceed $2\pi$ of the transmit frequency period. Since the continuous waves are narrow band, phase shifts (i.e., rotations) and/or phase delays may be used for beamforming steering continuous waves. For example, eight different phase shifts or delays are used for receive beamforming steered continuous waveforms. Each of the conceptual groupings of elements 24 represents one of eight different similar phase shift groupings. More or fewer than eight phase shift groupings may be used. The elements labeled P0 correspond to a zero phasing. The elements labeled P1 through P7 correspond to different relative phases.

Each element 24 is connected through a channel 26 to a combiner 28. The combiners 28 are nodes connecting a plurality of conductors, an amplifier, a summer, a digital combiner, an analog combiner, a multiplexer, combinations thereof or other now known or later developed structure for combining signals from a plurality of sources. The combiners 28 are part of the transducer assembly 12, such as being positioned within the probe housing 18. In alternative embodiments, the combiners 28 are positioned within the connector 20 or the receive beamformer 14. Each of the combiners 28 is operable to combine signals from a respective plurality of elements 24. The groupings of elements 24 correspond to subarrays within the transducer array 22. Eight different subarrays are formed in the embodiment of FIG. 1, resulting in eight different output signals for the transducer array 22. In alternative embodiments, additional or different numbers of subarrays and associated combiners 28 are provided. For example, the P1, P2 and P3 groupings with a greater number of elements are divided into two subarrays each. Each of the two subarrays has a same relative phase shift range.

In one embodiment, the transducer array 22 corresponds to a receive aperture, and different elements are provided for a transmit aperture, such as disclosed in U.S. Published Patent Application No. 2005-0203404, the disclosure of which is incorporated herein by reference. Any of symmetric or asymmetric distribution of the continuous wave transmit and receive apertures may be used. The transmit elements are part of the array 22 or part of a separate array. For example, one or more of the elements 24 of the transducer array 22 are used for transmit and the remaining elements 24 are used for receive operation. The combiners 28 are operable for receiving continuous wave signals.

Figure 3:
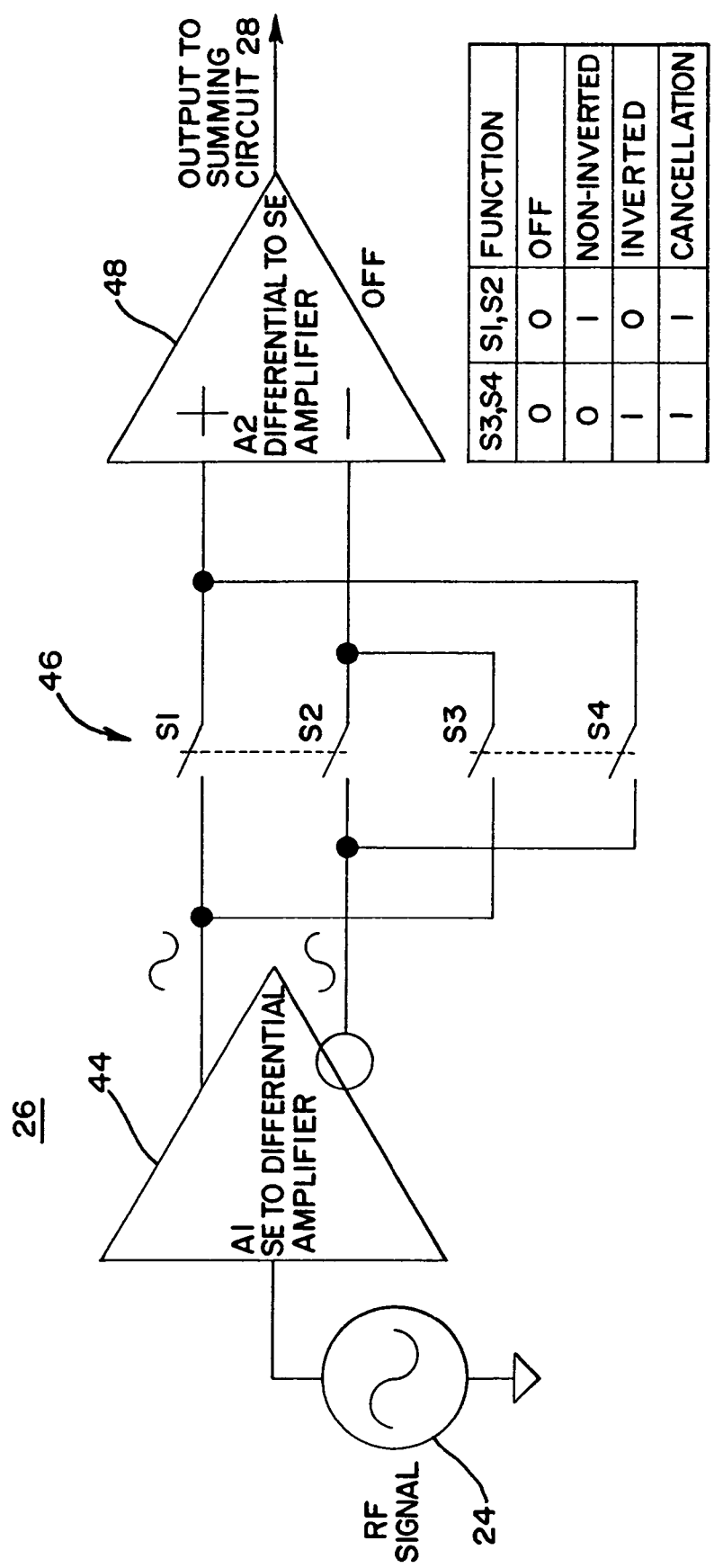
FIG. 3 is a block diagram of one embodiment of a pulsed and continuous wave switch network.

Each of the channels 26 is a conductor or other signal trace extending from an element 24 to a combiner 28. The channels 26 are free of switching during reception of continuous wave signals. In one embodiment, the channels 26 are free of switches or other active components. In other embodiments, the channels 26 include one or more switches that are operable to remain static for receiving continuous wave signals from the elements 24. For example, FIG. 3 shows one embodiment of a channel 26 connecting the transducer element 24 to the combiner 28. Such a circuit is disclosed in U.S. Published Patent Application No. 2005-0203392, the disclosure of which is incorporated herein by reference. The channel 26 includes a single input to differential output amplifier 44, a switch network 46 and a differential input to single-ended output amplifier 48. Additional, different or fewer components may be provided. The switch network 46 includes two pairs of transistor switches operable in response to two control signals, respectively. The differential output amplifier 44 provides inverted and non-inverted receive signals to each pair of switches 46. The single-ended output amplifier 48 outputs a signal responsive to the switches 46 and the input signal from the transducer element 24.

As shown in FIG. 3, the switches 46 may be configured in one of four different states: off, non-inverted, inverted and cancellation states. For continuous wave imaging, the switches are switched into a non-inverted or an inverted state and maintained static during reception of continuous wave signals. For pulse wave imaging, any of the off, non-inverted and inverted states are used. For example, pulse wave imaging makes use of mixing or time division multiplexing using the switches 46. For mixing, the switches 46 are switched between an inverted and non-inverted state in response to a local oscillating signal. The switches 46 mix the local oscillating control signal with the received pulse wave signal. Alternatively, the switches 46 operate between the off and non-inverted states for time division multiplexing. The switches are turned to the non-inverted state for a time slot associated with the particular element 24 and are otherwise maintained in an off state.

Figure 4:
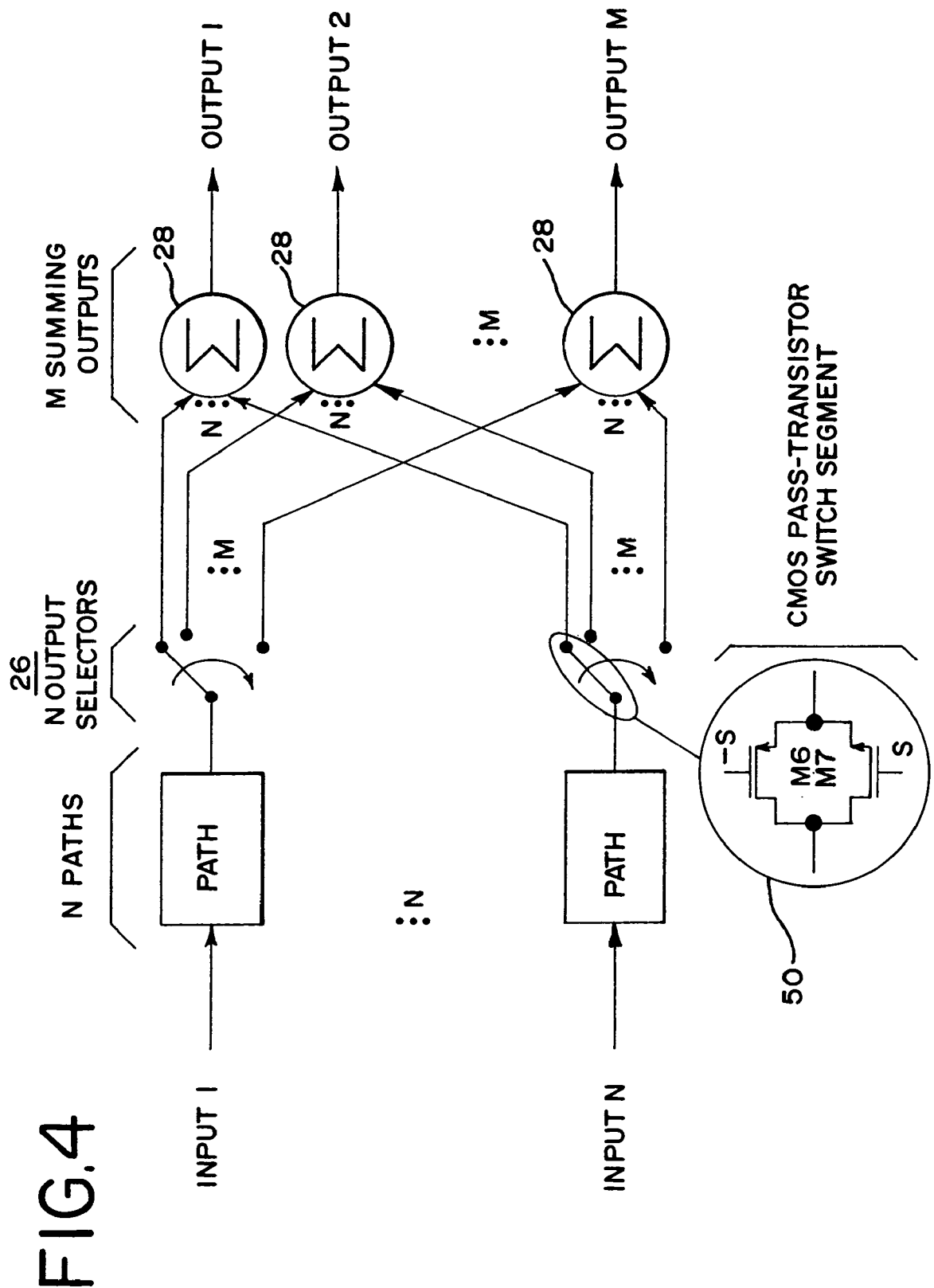
FIG. 4 is a block diagram of one embodiment of a switch network for continuous wave imaging.

In one embodiment, the subarrays of elements 24 associated with each combiner 28 are set or permanent. In another embodiment shown in FIG. 4, the channel 26 includes one or more switches 50 for selectively defining the subarrays. The switches 50 are transistors, CMOS pass transistors, pairs of transistors, Gilbert cells, relays, digital circuits, analog circuits, combinations thereof, or other now known or later developed switches. A switch 50 is provided for each possible connection of an element 24 to a different combiner 28, such as providing connections of each element 24 to one of eight different combiners 28. A fewer number of possible connections may be provided, such as where an element 24 is associated with a fewer number or sub-set of phase groupings. The switches 50 are operated prior to reception of continuous wave signals. Operation during reception may be provided. The switches 50 remain static during the combination of continuous wave signals to be used for imaging. The channels 26 include a plurality of path boxes. In this embodiment, each of the path boxes corresponds to the channel 26 shown in FIG. 3. In alternative embodiments, the channel 26 shown in FIG. 3 is used without the switches 50 of FIG. 4, or the switches 50 of FIG. 4 are used without the channel 26 of FIG. 3.

Additional or different structures may be provided for the channel 26. For example, U.S. Pat. No. 7,517,317, the disclosure of which is incorporated herein by reference, discloses forming super arrays for selecting between different subarray sizes for combining received signals. As disclosed therein, the combination structure using super arrays for switches different elements to different combiners, such as switching elements to one of four different combiners from each of multiple slices of the super array. By switching to different combiners, elements associated with a similar phase may be switched to a same combiner. Additional combiners combine the combined slice signals to form a complete subarray signal. For any given super array of elements, four outputs are provided associated with four different ranges of similar phase shift. Greater or fewer number of outputs and associated similar phase shift ranges may be provided.

Referring to FIG. 1, each of the subarrays or grouping of elements 24 corresponds to elements 24 associated with a similar phase shift. For example and as shown in FIG. 1, eight different phase shift ranges are provided. In this embodiment, a similar phase shift includes phase shifts within 45 degrees. As shown in FIG. 1, the center of each phase shift range is a 0, a $1/4\pi$, $1/2\pi$, $3/4\pi$, $\pi$, $5/4\pi$, $3/2\pi$ and $7/4\pi$. Larger or smaller phase shift ranges may be used with a same, greater or less number of combiners and associated outputs. For example, ten different combiners 28 are provided for ten different phase shift ranges of thirty-six degrees. In other embodiments, one or more of the combiners 28 is associated with a different size phase shift range. For example, one combiner 28 is associated with a 45 degree phase shift range, and a different combiner 28 is associated with a greater or lesser range of phase shifts. The phase shift is relative to the transmit frequency period. A similar phase shift is a relative term for distinguishing between at least two different values or ranges.

Figure 2:
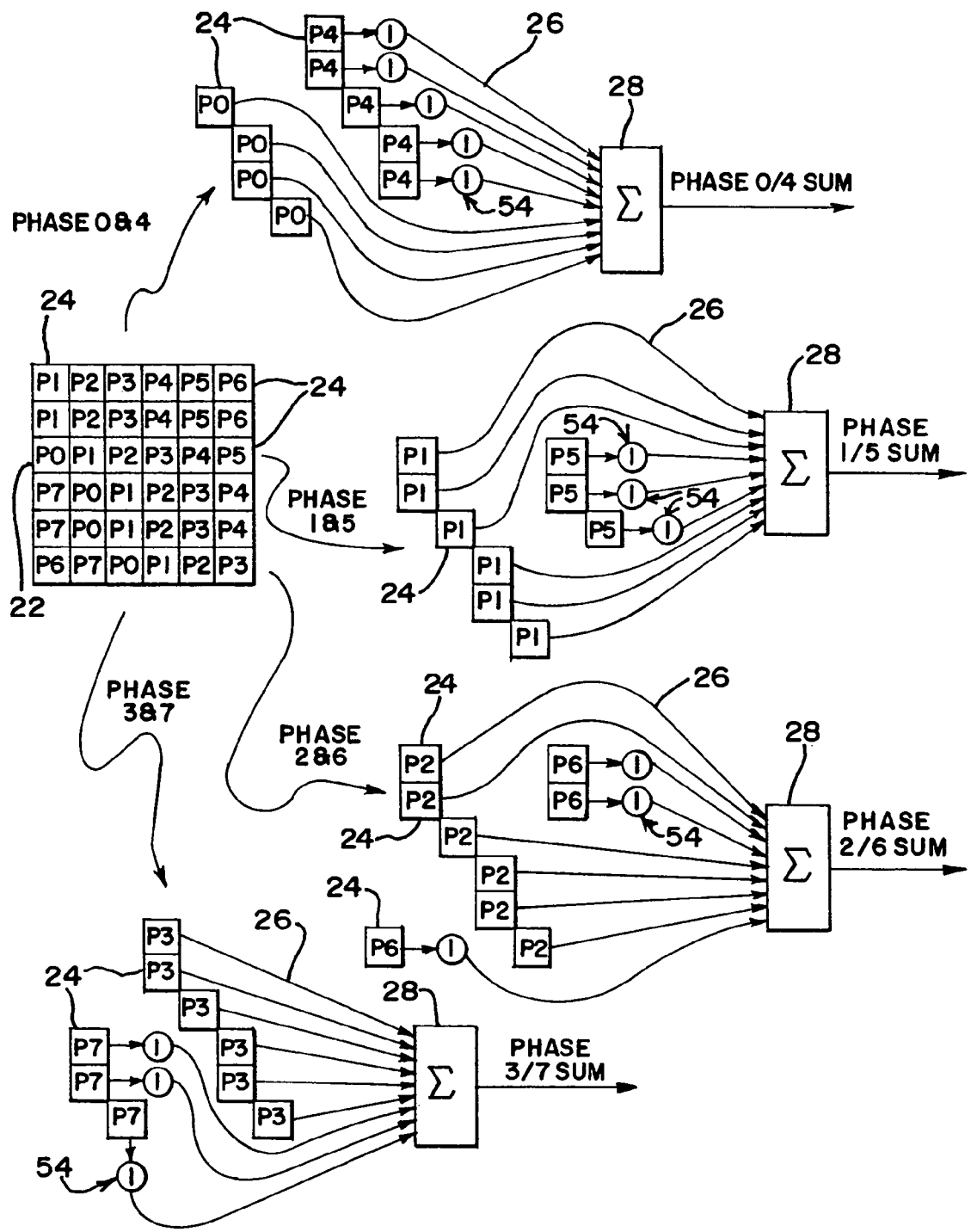
FIG. 2 is a graphical representation of another embodiment of combination of signals with similar phase.

FIG. 2 shows an embodiment with a reduced number of outputs for the same transducer array 22 and relative phasing shown in FIG. 1. Each of the subarrays of elements 24 associated with the combiner 28 corresponds to elements 24 with a similar phase shift and with phase shifts about 180 degrees from the similar phase shifts. For example, one combiner 28 is associated with the P0 and P4 elements for the phase shifts centered at 0 and $\pi$. Another combiner 28 is associated with the P1 and P5 elements 24 for 1/4 and $5/4\pi$ centered phase shifts. The phase shift ranges are of the same or different size for the two different ranges of similar phase shifts that are to be combined.

Inverters 54 invert the continuous wave signals associated with the elements 24 with the phase shifts of about 180 degrees from the other group of elements 24 to be combined. For example, the elements 24 labeled P4 are inverted for a combination with the elements labeled P0. The continuous wave signals from the elements 24 with a range of phase shifts centered at pi are inverted and combined with the non-inverted continuous wave signals from the elements 24 associated with the phase shift range centered at zero degrees. Each inverter 54 is an analog inverter, digital inverter, a differential output amplifier or other now known or later developed device for inverting signals. For example, each channel 26 includes the switch network 46 shown in FIG. 3. For continuous wave operation, the switches are either set to a non-inverted or an inverted state. Any of the signals from the different elements 24 may then selectively be inverted or not inverted for the combination. As a result, the eight different phase shift groupings are provided on four outputs. Alternatively, 16 different phase groupings are provided on 8 different outputs.

Any number of phase shift groupings and associated outputs may be used. FIGS. 1 and 2 show either all of the combiners 28 associated with a same phase shift range or with two different phase shift ranges. Combinations of a subset of the combiners of FIG. 2 associated with a single phase shift range with a subset of the combination of inverted and non-inverted signals may be used.

Where a different number of elements 24 are provided in each of the subarrays, amplifiers may be used to apply different amounts of amplification. Amplifiers include a pre-amplifier, the amplifier 44, the amplifier 48, an amplifier in one or more of the channels 26, an amplifier after the combiner 28, an amplifier in the receive beamformer 14 or other now known or later developed amplifiers. Different amounts of amplification are provided for continuous wave signals by amplifying prior to combination or by amplifying after combination. In one embodiment, the amplifiers are within the transducer assembly, such as amplifiers within the channels 26. The number of signals and associated elements 24 formed into a subarray may vary depending on the focus depth and steering angle. Subarrays or signal groups with fewer inputs may have increased amplifier gain to maintain constant headroom or dynamic range for the subarray. Alternatively, the same amplification is provided across the entire transducer array 22 or different amplifications but not as a function of the size of the subarray. After applying phase rotations or delays in the receive beamformer 14, gain differences may be removed before summation. Alternatively, gain differences between the subarrays are removed in the connector 20 prior to the receive beamformer 14.

For receive beamformation, the received subarray signals or summed continuous wave signals from different subarray groupings are relatively phased and combined. The relative phasing used corresponds to the phase shifts associated with the subarray. Where one or more of the combiners 28 is associated with no elements due to steering angle or focal depth, the receive beamformer sums the zero signal as part of the beamforming process. Alternatively to reduce noise, the combiners 28 associated with no subarray are not used for receive beamformation. Another alternative is to utilize unused combiners 28 to share the load of other combiners 28 that are heavily used.

Figure 5:
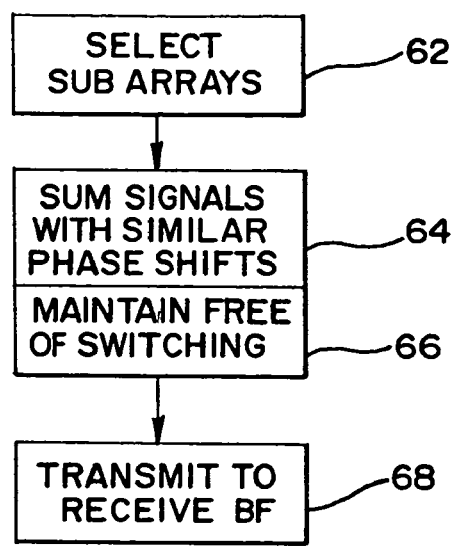
FIG. 5 is a flow chart diagram of one embodiment of a method for forming subarrays for continuous wave imaging.

FIG. 5 shows a method for selecting subarrays in continuous wave ultrasound imaging. Additional, different or fewer acts may be provided in a same or different order. The method is implemented by the systems described above or other systems.

In act 62, subarrays are selected for the receive aperture. For example, a first group of elements are selected. A second group of different elements are selected. Any number of groups of elements may be selected. In one embodiment, an entire receive aperture is formed into eight or four subarrays. In another embodiment, the entire receive aperture is divided into super arrays. Each super array outputs eight or four different outputs associated with different phase ranges. A plurality of outputs for the array has a same phase shift range. The selected elements form different subarrays. The elements included within each subarray are selected as a function of the steering angle and focal depth. As the steering angle or focal depth changes, the elements included in each subarray may change. The elements within a subarray may be contiguous or spaced from each other within the transducer array.

In act 64, the continuous wave signals for each of the subarrays are summed. Continuous wave signals received at the elements of a subarray corresponding to a range of phase shifts are summed. Summations for different phase shift ranges are performed for other groups of elements in other subarrays. Any of various sizes of phase shift ranges may be used. In one embodiment, continuous wave signals associated with two different ranges of phase shifts are combined. For example, the phase shifts between the groupings or ranges are about 180 degrees different. The continuous wave signals of one of the two groups of phase shift ranges are inverted prior to summation. The continuous wave signals from elements connected to the same combiners are summed. The elements connected to each combiner are associated with a similar phase shift. In one embodiment, more than one output and associated subarrays are provided for a same phase range.

In act 66, the continuous wave signals are maintained free of switching from the elements to summation. By preventing switching prior to summation, an increased dynamic range may be provided for the steered continuous wave signals. One or more switches may be positioned after each of the elements within one or more subarrays and prior to a combiner. The switches each have at least an open and a closed state. For example, switches for connecting different elements to different combiners as a function of the desired relative phase shift or switches for implementing pulsed wave functions are provided. The switches are maintained in a static position during reception of the continuous wave signals. For example, switches associated with routing a particular element to a desired combiner are maintained in a closed state during reception of the continuous wave signals. Switches for time division multiplexing, mixing or partial beamforming are maintained in a same state during reception of continuous wave signals.

The switches for pulsed wave processes may be moved between open and closed states during reception of pulsed wave signals in response to pulsed wave transmit events. For example, a transmitter generates pulsed wave transmit waveforms. The waveforms are applied to the transducer. Pulsed wave echo signals are received and mixed, multiplexed, partially beamformed or otherwise combined to form a fewer number of signals than elements. In a different transmit event, a different transmitter or the same transmitter generates continuous wave transmit waveforms for reception of continuous wave signals as described herein. In one embodiment, a continuous wave transmitter is provided in the transducer probe. In an alternative embodiment, the continuous wave transmitter is spaced from the transducer probe.

In act 68, the summed signals or outputs of the subarrays are transmitted separately to a receive beamformer. For example, the continuous wave signals within a subarray are summed together within a transducer probe. The summed outputs are transmitted to the receive beamformer, such as a continuous wave beamformer, in an imaging system spaced from the transducer probe by a cable. Alternatively, the outputs are transmitted to a continuous wave beamformer provided within a transducer probe or assembly. The summation forms subarray signals for different subarrays. By combining signals from a multi-dimensional or large transducer array, the number of channels or connections from the transducer probe to an imaging system is reduced.

In one embodiment, a same number of continuous wave signals are summed for each subarray. Alternatively, a different number of continuous wave signals are summed for different subarrays. The summed signals are provided to the receive beamformer with or without amplification. For example, a different amount of amplification is provided for one subarray than for another subarray.

In one embodiment, preamplification or buffering is provided within the transducer probe for each of the elements 24. The buffers or preamplifiers are selected to have large dynamic range, but may have a more limited dynamic range in other embodiments. Alternatively, preamplification and buffering is avoided for steered continuous wave imaging, but may be provided for pulsed wave imaging.

By reducing a number of outputs to correspond to the number of cables or receive beamformer channels or less, a multi-dimensional or large transducer array for four-dimensional imaging (i.e., real-time 3D imaging) may be used for pulsed wave imaging and still provide steered continuous wave imaging. Alternatively, the combination of subarrays for elements having similar phases is performed on a one-dimensional array or a two-dimensional array used for two-dimensional imaging.

Figure 6:
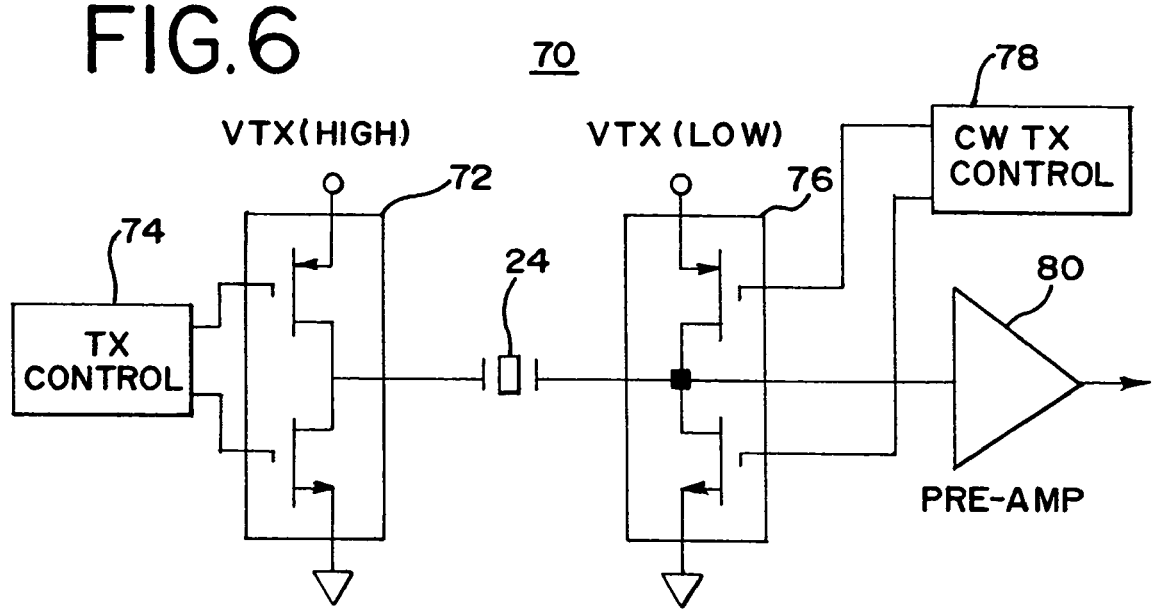
FIG. 6 is a circuit diagram of one embodiment of a transmitter circuit for pulsed and continuous wave imaging.

For use with the same or different transducer assembly 12 as discussed above, a continuous wave transmitter is shown in FIG. 6. FIG. 6 shows a transmit system 70 with a pulse wave transmitter 72 and associated control 74 and a continuous wave transmitter 76 and associated control 78. The pulsed and continuous wave transmitter 72 and 76 connect with an element 24. A preamplifier 80 connects with the element 24 as part of the receive channel. The transmit system 70 is used for each or a subset of the elements 24 of the array 22. Additional, different or fewer components may be provided. For example, the pulse wave transmitter 72 and associated control 74 are not provided. Both transmitters 72, 76 may be connected to a same side of the element 24. The system 70 provides for continuous wave transmission for ultrasound imaging.

The transducer element 24 has two sides, such as an upper and lower surface of a PZT element. Each side corresponds to an electrode. In one embodiment, one of the electrodes is connected to a relative ground potential, such as an absolute ground or a system ground. In the embodiment shown in FIG. 6, each side and associated electrode of the element 24 is connectable to ground through one or more switches. U.S. Pat. No. 6,806,623 (U.S. application Ser. No. 10/185,404), the disclosure of which is incorporated herein by reference, shows using the element for voltage isolation as shown in FIG. 6. A direct connection may be provided in other embodiments.

The pulse wave transmitter 72 includes two transistors and a high-voltage source. One transmitter connects from the high-voltage source to the element. The other transistor connects from the relative ground to the element. By alternately turning on and off the two transistors, a unipolar transmit waveform is generated. Switching networks for generating bipolar waveforms may alternatively be provided. The transmitter 72 is optimized for large voltage swings by a having a high voltage source, such as 100 to 200 volt source. A short number of cycles are provided for pulse wave transmission, such as four or fewer cycles. The interval between pulses is relatively long, such as 280 microseconds or more between pulses. A lesser or greater time period may be provided. For a four-cycle waveform at 2 MHz at an imaging depth of 20 centimeter, the 280 microseconds of roundtrip time including overhead results in a duty cycle of less than one percent. Other duty cycles may be provided. Additional, different or fewer components may be provided, such as providing a network or a greater number of transistors using one or more voltage sources.

The pulse wave transmitter 72 is connected with one side of the element 24. In one embodiment, the pulse wave transmitter 72 is provided within a transducer probe housing, but may alternatively be provided within a connector or an imaging system remote from the element 24.

The transmit control 74 for the pulse wave transmitter 72 is a digital or analog circuit. The transmit controller 74 is located within the transducer assembly 12 or within the imaging system. The transmit control 74 activates the transistors of the pulse wave transmitter 72.

The continuous wave transmitter 76 is two transistors and a low-voltage source. One transistor connects from the side of the element 24 opposite of the pulse wave transmitter 72 to ground. The other transistor connects from the same opposite side of the element 24 to the low voltage source. Additional transistors may be provided for bipolar or other waveform generation. In an alternative embodiment, the transistors of the continuous wave of transmitter 76 connect on the same side of the element 24 as the pulse wave transmitter 72. At least one transistor or voltage source of the continuous wave transmitter 76 is different than components of the pulse wave transmitter 72, providing a continuous wave transmitter separate from the pulse wave transmitter 72.

As shown in FIG. 6, the continuous wave transmitter 76 connects with the same electrode or same side of the element 24 as the receive circuitry and preamplifier 80. The element 24 acts to isolate the lower voltage components of the preamplifier 80 and the continuous wave transmitter 76 from the high voltage of the pulse wave transmitter 72. For example, the low voltage source of the continuous wave transmitter 76 is about five percent or less of the high voltage source. A greater or lesser voltage may be provided. Since the voltage is provided continuously for continuous wave imaging, regulations limit the voltage to be provided. Since the element 24 is used for either transmit or receive in continuous wave imaging, the continuous wave transmitter 76 may be provided on a same side or connected to a same electrode of the element 24 as the receive circuit and an associated preamplifier 80. The continuous wave transmitter 76 is located within a transducer probe housing, such as adjacent to the element 24.

The continuous wave transmit control 78 is a digital or analog device for controlling the transistors of the continuous wave transmitter 76. The transmit controller 78 is located within the transducer probe housing, the transducer assembly or the imaging device.

The continuous wave transmitter 76 is part of the transducer assembly associated with the element 24. For example, the continuous wave transmitter 76 is provided within a probe housing with the transducer array. The pulse wave transmitter 72 is within the probe housing or elsewhere. In one embodiment, the continuous wave transmitter 76 is integrated within an ASIC with the preamplifier 80 and/or other of the channels 26 and/or combiners 28 discussed above. A separate continuous wave transmitter 76 from the pulse wave transmitter 72 avoids having to switch or divide down the high voltage source of the pulse wave transmitter. Optimization of the components for low voltage operation within the continuous wave transmitter 76 may be provided, avoiding noise or power inefficiency due to components operable with high voltages of the pulse wave transmitter 72 being used for continuous wave imaging.

Figure 7:
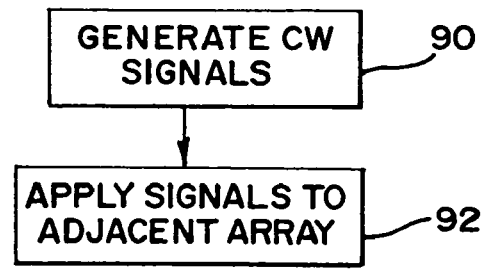
FIG. 7 is a flow chart diagram of one embodiment of a method for transmitting continuous waves.

FIG. 7 shows a method for transmission of continuous waves in ultrasound imaging. Additional, different or fewer acts may be provided in a same or different order. The method is implemented using the same system 70 shown in FIG. 6 above, but different systems or structures may be used. For example, a continuous wave transmitter is connected to one side of an element 24. A pulse wave transmitter is connected to a different side of the element 24. A receive channel is connected to the same side of the element of the continuous wave transmitter.

In act 90, continuous waves are generated with a continuous wave transmitter separate from a pulse wave transmitter. The separation includes at least one component being different, but shared components may be provided. Alternatively, no shared components are provided. In the system 70 shown in FIG. 6, the transistors of the continuous wave transmitter 76 are switched on and off in an alternating fashion. The transistor connected to ground of the pulse wave transmitter is switched on to the relative ground, and the transistor connected to the high voltage source is switched off. The switch to ground provides a grounding electrode for the element 24. Any receive signals from the preamplifier 80 are ignored. Alternatively, another switch disconnects the preamplifier from the element 24.

In act 92, signals are applied to the adjacent array. The continuous wave transmitter is housed within a same probe housing as the array. The generated continuous waves are applied to the transducer array to generate continuous wave acoustic signals. Different elements 24 are then used to receive echoes from the continuous wave signals.

For pulsed wave imaging, the transistors of the continuous wave transmitter 76 are turned off during receive time. The preamplifier 80 amplifies the received signals for further processing. The element 24 shields the preamplifier 80 from the high voltage swings of the pulse wave transmitter 72. The transistor connected to ground of the continuous wave transmitter 76 on a same side of the element 24 of the preamplifier 80 is turned on during transmit time. Any large voltage swings are shunted to ground, but low voltage swings due to received signals are passed to the preamplifier 80.

While the invention has been described above by reference to various embodiments, it should be understood that many changes and modifications can be made without departing from the scope of the invention. For example, the continuous wave transmitter is used without or with the subarray formation of elements with similar phase shifts and vice versa.

It is therefore intended that the foregoing detailed description be regarded as illustrative rather than limiting, and that it be understood that it is the following claims, including all equivalents, that are intended to define the spirit and scope of this invention.

We claim:

1. A system for selecting subarrays in continuous wave ultrasound imaging, the system comprising:
   a transducer array as part of a transducer assembly, the transducer array having a plurality of elements;
   a plurality of combiners as part of the transducer assembly, each of the combiners configured to combine signals from a respective plurality of elements corresponding to a subarray;
   wherein channels from the plurality of elements to the plurality of combiners are configured to be free of switching during reception of continuous wave signals; and
   a plurality of switches within the channels, the switches configured to select between connection of each of the plurality of elements to different ones of the plurality of combiners, the selection corresponding to the subarrays, the switches configured to select prior to combination of the continuous wave signals and configured to remain static during combination of the continuous wave signals.

2. The system of claim 1 wherein the transducer array comprises a multi-dimensional array.

3. The system of claim 1 wherein the transducer assembly comprises a transducer probe housing, both the transducer array and the plurality of combiners at least partially within the transducer probe housing.

4. The system of claim 1 further comprising:
   a plurality of switches operable to define the subarrays, each of the subarrays corresponding to elements of the plurality of elements having a similar phase shift.

5. The system of claim 1 wherein the subarrays correspond to elements of the plurality of elements having a similar phase shift.

6. The system of claim 1 wherein the subarrays correspond to elements of the plurality of elements with similar phase shifts and with phase shifts about 180 degrees from the similar phase shifts.

7. The system of claim 6 further comprising:
   a plurality of inverters operable to invert the continuous wave signals of the elements with the phase shifts about 180 degrees from the similar phase shifts.

8. The system of claim 1 further comprising:
   a plurality of amplifiers operable to apply different amounts of amplification for continuous wave signals associated with different subarrays, the plurality of amplifiers being part of the transducer assembly.

9. The system of claim 1 further comprising:
   at least one switch for each of the channels and corresponding elements of the plurality of element elements, the switch configured to remain static for receiving continuous wave signals from the respective element and configured to perform one of: mixing and multiplexing for pulsed wave signals from the respective element.

10. The system of claim 1 further comprising:
    a high voltage transmitter connected with the plurality of elements; and
    a low voltage transmitter as part of the transducer assembly connected with the plurality of elements.

11. A method for selecting subarrays in continuous wave ultrasound imaging, the method comprising:
    (a) summing continuous wave signals from a first plurality of elements of an array corresponding to a first range of phase shifts;
    (b) summing continuous wave signals from a second plurality of elements of the array corresponding to a second range of phase shifts different than the first range; and
    (c) transmitting the outputs of (a) and (b) separately to a receive beamformer.

12. The method of claim 11 further comprising:
    (d) maintaining the continuous wave signals free of switching from the first and second pluralities of elements through summation.

13. The method of claim 11 wherein (a) and (b) are performed within a transducer probe and the receive beamformer comprises a continuous wave beamformer in an imaging system spaced from the transducer probe by a cable.

14. The method of claim 11 further comprising:
    (d) selecting the first plurality of elements as a function of a steering angle; and
    (e) selecting the second plurality of elements as a function of the steering angle.

15. The method of claim 11 wherein (a) comprises summing continuous wave signals of the first range of phase shifts with inverted continuous wave signals having phase shifts about 180 degrees from the first range of phase shifts.

16. The method of claim 11 wherein (a) and (b) comprises forming subarray signals for first and second subarrays, respectively, of a multi-dimensional transducer array.

17. The method of claim 11 wherein a different number of the continuous wave signals are summed in (a) than in (b); further comprising:
    (d) amplifying associated with (a) differently than with (b) as a function of the different number.

18. The method of claim 11 wherein at least one switch is positioned after each of the elements of the first and second pluralities of elements and prior to a combiner performing the summations of (a) and (b), each switch having an open and a closed state;
    further comprising:
    (d) maintaining each switch at the closed state or open state during reception of the continuous wave signals in response to a first continuous transmit event; and (e) moving the switches between the open and closed states during reception of pulsed wave signals in response to a second pulsed transmit event.

19. The method of claim 11 further comprising:

(d) generating continuous wave transmit waveforms with a first transmitter in a transducer probe, (a) and (b) being performed in the transducer probe;

(e) generating pulsed wave transmit waveforms with a second transmitter.

20. A system for transmission of continuous waves in ultrasound imaging, the system comprising:

a transducer array;

a pulsed wave transmitter connectable with the transducer array;

a continuous wave transmitter connectable with the transducer array, the continuous wave transmitter separate from the pulsed wave transmitter.

21. The system of claim 20 further comprising:

a probe housing, the transducer array and the continuous wave transmitter within the probe housing.

22. The system of claim 21 wherein the pulsed wave transmitter is within the probe housing.

23. The system of claim 20 wherein the transducer array comprises at least one transducer element having first and second sides, the pulsed wave transmitter connectable with the first side and the continuous wave transmitter connectable with the second side.

24. The system of claim 23 further comprising:

a receiver pre-amplifier connected with the second side.

25. The system of claim 23 wherein the pulsed wave transmitter comprises first and second transistors, the first transistor connected between the first side and a high power voltage source, the second transistor connected between the first side and a relative ground potential; and wherein the continuous wave transmitter comprises third and fourth transistors, the third transistor connected between the second side and a low power voltage source, the fourth transistor connected between the second side and the relative ground potential.

26. A method for transmission of continuous waves in ultrasound imaging, the method comprising:

providing a continuous wave transmitter and a pulsed wave transmitter;

(a) generating continuous waves with the continuous wave transmitter separate from the pulsed wave transmitter;

(b) applying the continuous waves to a transducer array within a same probe housing as the continuous wave transmitter.

27. The method of claim 26 further comprising:

(c) connecting the continuous wave transmitter to a first side of an element; and (d) connecting the pulsed wave transmitter to a second side of the element.

28. The method of claim 27 further comprising:

(e) connecting a receive channel to the first side of the element.

\* \* \* \* \*